United States Patent
Kahen

(10) Patent No.: US 10,456,422 B2
(45) Date of Patent: Oct. 29, 2019

(54) SURGICAL WOUND HEALING COMPOSITION AND METHOD OF APPLYING THE SAME

(71) Applicant: Payam John Kahen, Beverly Hills, CA (US)

(72) Inventor: Payam John Kahen, Beverly Hills, CA (US)

(*) Notice: Subject to any disclaimer, the term of this patent is extended or adjusted under 35 U.S.C. 154(b) by 0 days.

(21) Appl. No.: 15/672,048

(22) Filed: Aug. 8, 2017

(65) Prior Publication Data

US 2018/0050066 A1 Feb. 22, 2018

Related U.S. Application Data

(60) Provisional application No. 62/377,485, filed on Aug. 19, 2016, provisional application No. 62/376,803, filed on Aug. 18, 2016.

(51) Int. Cl.

| | |
|---|---|
| *A61K 35/19* | (2015.01) |
| *A61K 9/10* | (2006.01) |
| *A61K 9/00* | (2006.01) |
| *A61K 31/58* | (2006.01) |
| *A61K 35/12* | (2015.01) |
| *A61K 35/16* | (2015.01) |
| *A61B 5/00* | (2006.01) |
| *A61B 17/00* | (2006.01) |
| *A61B 18/00* | (2006.01) |

(52) U.S. Cl.
CPC ............ *A61K 35/19* (2013.01); *A61K 9/0019* (2013.01); *A61K 9/10* (2013.01); *A61K 31/58* (2013.01); *A61K 35/12* (2013.01); *A61K 35/16* (2013.01); *A61B 5/448* (2013.01); *A61B 2017/00752* (2013.01); *A61B 2018/00476* (2013.01)

(58) Field of Classification Search
CPC ........ A61K 35/38; A61K 47/46; A61K 35/12; A61K 31/58; A61K 9/0019; A61K 9/10; A61K 35/16; A61K 35/19; A61K 2300/00
See application file for complete search history.

(56) References Cited

U.S. PATENT DOCUMENTS

| | | |
|---|---|---|
| 9,173,921 B1 | 11/2015 | Lim |
| 9,227,089 B1 | 1/2016 | Greco et al. |
| 2008/0138324 A1* | 6/2008 | Kleinsek ............ A61K 38/1808 424/93.7 |

OTHER PUBLICATIONS

Gkini et al. Study of Platelet-Rich Plasma Injections in the Treatment of Androgenetic Alopecia Through an One-Year Period. Journal of Cutaneous and Aesthetic Surgery (2014), v7(4), p. 213-219. (Year: 2014).*

(Continued)

*Primary Examiner* — Sean C. Barron
(74) *Attorney, Agent, or Firm* — Stetina Brunda Garred and Brucker

(57) ABSTRACT

Compositions and methods are disclosed for improving the healing of surgical wounds, and specifically for improving the survival rate, color retention rate, density, and scarring rate of a hair follicular graft following a hair transplantation surgery. The composition may be a suspension for injection proximal to the surgical graft recipient site, with the suspension comprising 0.4-0.5 mL of a suspension of an autologous platelet solution of at least 1 billion platelets at a concentration exceeding 1.5 billion platelets per mL, about 20 mg of granulated extracellular matrix, and about 40 mg of triamcinolone acetonide.

15 Claims, 1 Drawing Sheet

(56) References Cited

OTHER PUBLICATIONS

Uebel et al. The Role of Platelet Plasma Growth Factors in Male Pattern Baldness Surgery. Plast. Reconstr. Surg. 118: 1458-1466, 2006 (Year: 2006).*

G.S. Hitzig. Early results in the use of injectable ACell suspended in arterial blood serum/PRP in retarding hair loss/re-growth of miniaturizing scalp hairs. Hair Transplant Forum International (May-Jun. 2011), p. 73-74 (Year: 2011).*

M. Kumaresan. Intralesional Steroids for Alopecia Areata. Int J Trichology. Jan.-Jun. 2010; 2(1): 63-65 (Year: 2010).*

Rommer et al. Urinary Bladder Matrix for the Treatment of Recalcitrant Nonhealing Radiation Wounds. Adv Skin Wound Care (2013), v26, p. 450-455. (Year: 2013).*

Matristem® Micromatrix. Product manual (2012), 2 pages. (Year: 2012).*

J.E. Cooley. Use of porcine urinary bladder matrix in hair restoration surgery applications. Hair Transplant Forum International (May-Jun. 2011), p. 65 and p. 71-72 (Year: 2011).*

S.F. Badylak. Xenogeneic extracellular matrix as a scaffold for tissue reconstruction. Transplant Immunology (2004), v12, p. 367-377 (Year: 2004).*

Nofal et al. Platelet-Rich Plasma Versus CROSS Technique With 100% Trichloroacetic Acid Versus Combined Skin Needling and Platelet Rich Plasma in the Treatment of Atrophic Acne Scars: A Comparative Study. Dermatol Surg 2014;40:864-873. (Year: 2014).*

Lyakhowitsky et al. Frontal fibrosing alopecia update. World Journal of Dermatology (2015), 4(10, 33-43. (Year: 2015).*

Alves, Rubina MD. and Grimalt, Ramon MD, PHD. "Randomized Placebo-Controlled, Double-Blind, Half-Head Study to Assess the Efficacy of Platelet-Rich Plasma on the Treatment of Androgenetic Alopecia". Dermatologic Surgery, vol. 42 Issue 4. Apr. 2016. pp. 491-497.

Department of Periodontics, Harvard School of Dental Medicine, Boston, MA 02115. "Role of Platelet Derived Growth Factor in Wound Healing: Synergistic Effects with Other Growth Factors" Proc. Natl. Acad. Sci. USA, vol. 84. Nov. 1987. pp. 7696-7700. Medical Sciences. <http://www.ncbi.nlm.nih.gov/pmc/articles/PMC299367/>.

"MatriStem MicroMatrix". ACell Inc. 2016.

Ramos-Torrecillas, Javier PhD; Luna-Bertos, Elvira De PhD; García-Martínez, Olga PhD; Ruiz, Concepción PhD. "Clinical Utility of Growth Factors and Platelet Rich Plasma in Tissue Regeneration: A Review". Wounds a Compendium of Clinical Research and Practice, vol. 26 Issue 7. Jul. 2014. pp. 207-213.

Kahen, John MD. "The Use of Platelet Rich Plasma in Treating Hair Loss". International Society of Hair Restoration Surgery, vol. 25 Issue 5. Sep. 2015. <http://www.ishrs.org/content/use-platelet-rich-plasma-treating-hair-loss>.

Cole, John P. MD. and Wolf, Bradley R. MD. "Cyberspace Chat— Platelet Rich Plasma (PRP): Pseudoscience or Fact." Hair Transplant Forum International, vol. 25 Issue 3. May/Jun. 2015. pp. 110-114.

\* cited by examiner

SURGICAL WOUND HEALING COMPOSITION AND METHOD OF APPLYING THE SAME

CROSS-REFERENCE TO RELATED APPLICATIONS

This application relates to and claims the benefit of U.S. Provisional Application No. 62/376,803 filed Aug. 18, 2016 entitled "SURGICAL WOUND HEALING COMPOSITION AND METHOD OF APPLYING THE SAME," the entire disclosure of which is hereby wholly incorporated by reference, and U.S. Provisional Application No. 62/377,485 filed Aug. 19, 2016 entitled "SURGICAL WOUND HEALING COMPOSITION AND METHOD OF APPLYING THE SAME." the entire disclosure of which is hereby wholly incorporated by reference.

STATEMENT RE: FEDERALLY SPONSORED RESEARCH/DEVELOPMENT

Not Applicable

BACKGROUND

1. Technical Field

The present disclosure relates generally to methods and compositions for facilitating wound healing, and more particularly to methods and compositions for improving outcomes following epidermal and/or dermal surgical procedures, such as hair transplantations.

2. Related Art

There exists great interest in the medical community in the potential applications of platelet-rich plasma (PRP) as a clinical tool in many types of therapies. PRP is typically formed by extracting a volume of patient's blood, adding an anticoagulation agent, centrifuging that blood to remove red blood cells, and possibly taking further action to enrich the concentration of platelets and/or other remaining components within the plasma. While, the circulating blood of a healthy patient typically contains about two hundred million platelets per mL, FDA-approved methods for forming PRP concentrate generally result in about a five-fold increases in platelet concentration, to around one billion platelets per mL. Additionally, the process for forming PRP may increase the concentration of the circulating growth factors, cytokines, and leukocytes above the levels found in whole blood.

However, a number of deficiencies and misunderstandings currently exist in the field of PRP-based therapies, especially among therapies involving autologous grafting or healing of surgical wounds. An uptick in media coverage fueled by endorsement by professional athletes of various PRP-based therapies of questionable benefit has exacerbated this confusion, often causing medical practitioners and the public at large to misunderstand the benefits of PRP therapies, and to attribute a panacea of benefits to the basic therapy of injecting PRP by itself, when often such therapies may have little or no clinical efficacy.

Thus, there exists a need in the art for novel compositions and methods incorporating PRP.

BRIEF SUMMARY

To solve these and other problems, methods and compositions for facilitating healing of wounds are contemplated. In an exemplary embodiment of such compositions and methods, a ternary fusion of platelet-rich plasma, granulated extracellular matrix, and triamcinolone acetonide is prepared for application to surgical wounds. The combination of these components, when applied at graft recipient sites following creation of those sites, has been found to result in a supra-additive effect which reduces the propensity of wounds to develop keloid or hypertrophic scars, reduces inflammation and swelling, and increases the survival rate of the transplanted graft. Such compositions have been found to be especially useful for improving the survival rate and color pigmentation retention rate of transplanted follicles following hair transplantation surgery, and in reducing scarring at both the donor and recipient sites.

The composition for facilitating healing of a wound may be, according to one embodiment, a suspension comprising an autologous platelet solution above basal concentration, a granulated extracellular matrix; and triamcinolone acetonide. It is contemplated that the concentration of the autologous platelet solution may exceed 1.5 billion platelets per ml, and may be injected proximal to the wound.

It is further contemplated that according to certain embodiments, the autologous platelet solution, the granulated extracellular matrix, and the triamcinolone acetonide may be combined into a suspension and injected proximal to the wound. According to one exemplary embodiment, such a suspension may comprise about 1 billion autologous platelets, about 20 mg granulated extracellular matrix, and about 40 mg triamcinolone acetonide. The granulated extracellular matrix may be autologous or non-autologous.

Various methods and methodologies in which such compositions may be utilized are also contemplated, such as methods in which the compositions are applied via injection directly at an opening of the wound. One exemplary method contemplated is one in which embodiments of the above described composition may be injected proximal to the recipient site of a hair follicular graft taken from a donor site during a hair transplantation surgery, such as follicular unit transplantation or follicular unit extraction. In such a method, is further contemplated that the injection may comprise injecting at a plurality of injection sites spaced about 1 cm apart, with each injection comprising about 0.4-0.5 mL of a suspension as described above.

BRIEF DESCRIPTION OF THE DRAWINGS

These and other features and advantages of the various embodiments disclosed herein are better understood with respect to the following descriptions and drawings, in which.

DETAILED DESCRIPTION

Figure 1:
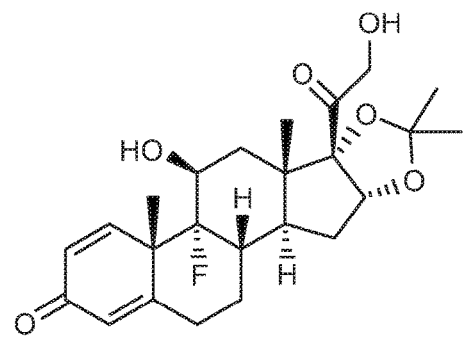
FIG. 1 is an image of the synthetic corticosteroid triamcinolone acetonide.

According to various aspects of the present disclosure, compositions and methods are disclosed for healing of wounds, with an exemplary composition suitable for improving the survival rate of a hair follicular graft during a hair transplantation surgery being a suspension for injection proximal to the recipient site following creation of that recipient site, with the injection comprising 0.4-0.5 mL of a suspension of an autologous platelet solution of at least 1 billion platelets at a concentration exceeding 1.5 billion platelets per mL, about 20 mg of granulated extracellular matrix, and about 40 mg of triamcinolone acetonide. It has been found that the application of the herein disclosed compositions proximal to a surgical wound such as a graft donor or graft recipient site, according to the herein disclosed protocols, may result in improved wound healing attributes, and in the context of hair transplantation surgeries, may result in an improved survival rate of grafts, an improved color pigmentation of the transplanted hair grafts, and a greatly reduced scarring rate.

According to one exemplary embodiment of the present disclosure, an autologous platelet solution above basal concentration is contemplated as being a component of a suspension for healing of a wound. As basal concentration is the level of platelets in whole blood, which is generally within the range of 150,000 to 350,000 platelets per µL, a solution above basal concentration would thus be formed by any method which increases the concentration of platelets within the autologous whole blood solution of the particular patient. Methods known in the art for increasing platelet concentration include, for example but without limitation, a process including the steps of collection of whole blood, addition of an anticoagulant such as adenosine citrate dextrose-acid, centrifugation at a speed optimized to collect red blood cells in a pellet, and removal of the red blood cell pellet. However, it may be seen that any process that results in the product of an autologous platelet solution above basal concentration is contemplated as within the scope of the present disclosure. Current centrifuge systems on the market capable of creating an autologous platelet solution above basal concentration include, for example, the Harvest smartPrep Mixing Platelet Centrifuge system.

Additionally, it may be seen that an autologous platelet solution that is derived from whole blood may additionally contain various whole blood components such as growth factors, cytokines, and leukocytes. Such growth factors, which may or may not be cytokines as well, may include, for example, Platelet Derived Growth Factor (PDGF) or Vascular Endothelial Growth Factor (VEGF). Leukocytes may include, for example, lympohocytes, granulocytes, monocytes, and macrophages.

In the above stated exemplary embodiment, the autologous platelet solution above basal concentration is prepared by extracting 54 mL of peripheral blood from the patient via a platelet concentrated syringe which transfers the blood to a plastic tube container. The blood is fused with 2 mL of 3.8% sodium citrate, an anticoagulant. 20 mL of citrated blood is inserted into a centrifuge and centrifuged a first time to separate the red blood cells from the remaining platelet/white blood cell volume. The red blood cell layer or pellet is removed, and the remainder is spun again to form a soft erythrocyte-platelet pellet at the bottom of the tube. The upper portion of the volume is removed, and the remaining pellet is homogenized in the lower portion of the volume to create a platelet-rich plasma.

It is additionally contemplated that according to the above stated exemplary embodiment, granulated extracellular matrix (ECM) is included as a component of a suspension for healing of a wound. Generally, granulated extracellular matrix is comprised of macroscopic particles of extracellular matrix derived from a donor, and preferably an animal donor, such as in the case of porcine-derived extracellular matrix, which is one of the most common sources in the market today. According to the above stated exemplary embodiment, granulated animal ECM scaffolding from the porcine small intestinal submucosa is utilized. However, it may be seen that other sources of ECM may be used, such as human skin, dermis, or fascia lata, including allografts, bovine or equine pericardium, fetal bovine skin, or other porcine ECM components such as porcine dermis, skin, or urinary bladder matrix. Porcine small intestinal submucosa is comprised of, by dry weight, more than 90% collagen, with the majority being collagen type I, with minor amounts of collagen types III, IV, V, and VI. Porcine small intestinal submucosa may also contain a variety of glycosaminoglycans, including heparin, heparin sulfate, chondroitin sulfate, and hyaluronic acid, as well as a variety of adhesion molecules or proteins such as fibronectin, laminin, decorin, biglycan, and entactin. Porcine small intestinal submucosa may also contain various growth factors such as transforming growth factor-β, basic fibroblast growth factor, and vascular endothelial growth factor.

In the above stated exemplary embodiment, it is contemplated that the porcine small intestinal submucosa is dried and finely granulated to a powder consistency, and suspended with the composition. According to certain more particular embodiment, for a single application of the suspension, about 20 mg of granulated ECM may suspended within a solution of about 1 billion autologous platelets at a concentration of platelets exceeding 1.5 billion platelets per mL. A single application for injection proximal to a surgical wound may comprise, for example, about 0.4 to 0.5 mL of suspension per injection. Granulated ECM may be extracted, dried, and granulated, or may be obtained commercially from manufacturers such as Lifecell, Bard, TEI Biosciences, Cook SIS, or ACell.

It is additionally contemplated that according to the above stated exemplary embodiment, triamcinolone acetonide may be included as a component of a suspension for healing of a wound. Triamcinolone acetonide, also called 9α-fluoro-16α-hydroxyprednisolone 16α,17α-acetonide, is a synthetic corticosteroid having the molecular formula as shown in FIG. 1. Triamcinolone acetonide is commercially used as an immunosuppressant administered via topical, injectable, or nasal spray routes for mitigating inflammation or blistering, and in controlling severe allergic states, and is generally available under the brand names Kenalog or Volon A.

In the above stated more particular embodiment, for a single application via injection proximal to the wound of about 0.4-0.5 mL of the suspension, about 40 mg of triamcinolone acetonide is included. However, it may be seen that in other embodiments, more or less triamcinolone acetonide may be used, and it may further be seen that in some embodiments, triamcinolone actinide may be omitted entirely, such as, for example, when certain of the herein contemplated embodiments may be utilized with patients having allergies or other conditions for which the application of triamcinolone acetonide may not be suitable.

It may be seen that application of the embodiments of the presently disclosed compositions according to the presently disclosed methods may result in substantial benefits, including but not limited to mitigation of scar tissue. Keloid or hypertrophic scars, which result from the overgrowth of scar tissue over the top layer of skin, may cause substantial pain and may appear unpleasant.

One exemplary method of applying the presently disclosed compositions is via injection into a recipient area, including but not limited to a surgical graft recipient site. Recipient sites, for example include, but are not limited to incisions that are made for the insertion of hair follicles during a hair transplant. According to this exemplary embodiment of a method, the recipient area is first disinfected, such as with a povidone-iodine antiseptic. The recipient area is then anesthetized with a local anesthetic such as a 1% lodicaine solution along with 1:100,000 of epinephrine using a ring block technique. Immediately prior to, concurrent with, or after placement of the graft at the recipient site, embodiments of the presently disclosed composition may be injected at a spacing of about 1 cm apart using a 27-gauge needle in a 1 cc tuberculin Luer-lock syringe into the intradermal/subdermal layers of recipient area, with each injection being about 0.4-0.5 mL of the composition. Depending on the particular recipient area chosen and the patient, however, it may be seen that variation of such a method may include, for example, the use of smaller or larger gauge needles. It may also be seen that many other variations of such a method may exist, in which the presently disclosed compositions are applied according to different methods of administration.

Figure 2:
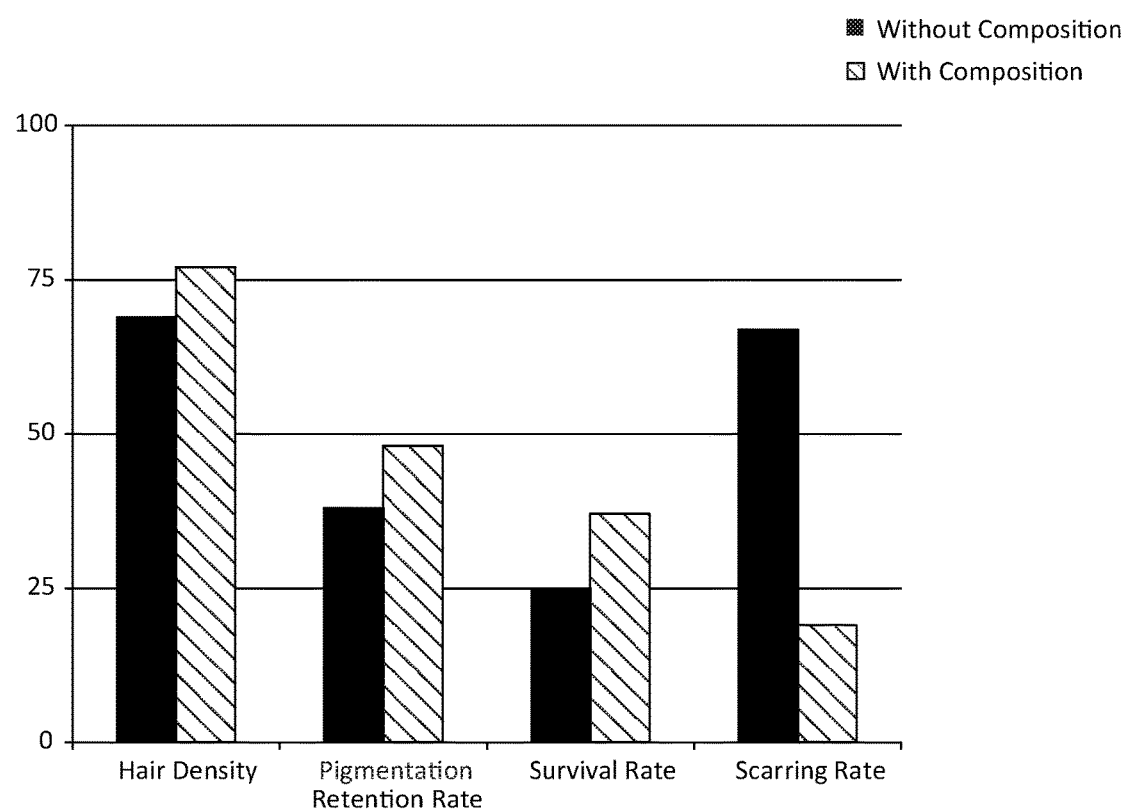
FIG. 2 is a table showing experimental results of administrations of embodiments the herein disclosed compositions.

As shown in the table of FIG. 2, it may be seen that following experimental administrations of the above disclosed certain more particular embodiment according to the above disclosed exemplary method in the context of a hair follicular graft, it was observed that the resulting hair follicular grafts displayed hair density, survival rates, and color pigmentation retention rates far above the levels expected absent the application of the presently disclosed compositions, and it was further observed that the scarring rate was substantially reduced. It is understood that these results are due to a synergistic effect of the components of the herein disclosed compositions that goes beyond what would be expected from a mere addition of their known properties, which renders the presently disclosed compounds. These outcomes are seen not only in the context of scalp hair follicular grafts, but in all hair transplant surgeries with which the herein disclosed compositions have been utilized, including but not limited to eyebrow and beard transplants.

It is believed that such results are due to a combination of factors, including the promotion of the dermal papilla cell reproduction due to the interaction of the components of the suspension with the dermal papillar cells, which results in the shifting of the cells of the hair follicles to the anagen phase. Further, it is understood that such results may also be due to the anti-inflammatory aspects of the disclosed compositions, which may protect the capillary veins of the patient from damage from the surgical wound, reducing the risk of hemorrhage, and correspondingly reducing the rate of scarring. It is additionally understood that the keratinocyte cells may be activated by the application of the herein disclosed compositions, which may greatly increase the survival rate of hair follicle grafts.

The above description is given by way of example, and not limitation. Given the above disclosure, one skilled in the art could devise variations that are within the scope and spirit of the disclosure herein. Further, the various features of the embodiments disclosed herein can be used alone, or in varying combinations with each other and are not intended to be limited to the specific combination described herein. Thus, the scope of the claims is not to be limited by the exemplary embodiments.

What is claimed is:

1. A method for improving the survival rate of a hair follicular graft during a hair transplantation surgery from a donor site to a recipient site, the method comprising injecting, proximal to the recipient site, a therapeutically effective amount of a suspension comprising:
   an autologous platelet solution above basal concentration;
   granulated extracellular matrix; and
   triamcinolone acetonide;
   wherein administration of the therapeutically effective amount of the suspension is operative to decrease the scarring rate at the recipient site by more than 50%, increase the pigmentation retention rate of the hair follicular graft, and increase the survival rate of the hair follicular graft.

2. The method of claim 1, wherein the autologous platelet solution exceeds 1.5 billion platelets per mL.

3. The method of claim 1, wherein the suspension comprises a volume of 0.4 to 0.5 ml containing about 1 billion autologous platelets, about 20 mg granulated extracellular matrix, and about 40 mg triamcinolone acetonide.

4. The method of claim 1, wherein injecting proximal to the recipient site comprises injecting at a plurality of injection sites spaced about 1 cm apart.

5. The method of claim 4, wherein each injection at the plurality of injection sites comprises about 0.4 to 0.5 mL of the suspension.

6. The method of claim 1, wherein the hair transplantation surgery comprises follicular unit transplantation.

7. The method of claim 1, wherein the hair transplantation surgery comprises follicular unit extraction.

8. A method for facilitating healing of a hair follicular graft recipient site, the method comprising applying proximal to the hair follicular graft recipient site a therapeutically effective amount of a suspension comprising:
   an autologous platelet solution above basal concentration;
   granulated extracellular matrix; and
   triamcinolone acetonide;
   wherein administration of the therapeutically effective amount of the suspension is operative to decrease the scarring rate at the recipient site by more than 50%, increase the pigmentation retention rate of the hair follicular graft, and increase the survival rate of the hair follicular graft.

9. The method of claim 8, wherein the concentration of the autologous platelet solution exceeds 1.5 billion platelets per mL.

10. The method of claim 8, wherein the suspension solution is injected proximal to the hair follicular graft recipient site.

11. The method of claim 8, wherein the autologous platelet solution, the granulated extracellular matrix, and the triamcinolone acetonide are combined in a suspension and injected proximal to the hair follicular graft recipient site.

12. The method of claim 11, wherein the suspension injected proximal to the hair follicular graft recipient site comprises a volume of 0.4 to 0.5 ml containing about 1 billion autologous platelets, about 20 mg granulated extracellular matrix, and about 40 mg triamcinolone acetonide.

13. The method of claim 11, wherein the suspension is injected directly at the hair follicular graft recipient site.

14. The method of claim 8, wherein the granulated extracellular matrix is autologous.

15. The method of claim 8, wherein the granulated extracellular matrix is non-autologous.

* * * * *